(12) United States Patent
Habermann et al.

(10) Patent No.: US 7,939,293 B2
(45) Date of Patent: May 10, 2011

(54) METHOD FOR PRODUCING CARBOXY-TERMINAL-AMIDIFIED PEPTIDES

(75) Inventors: Paul Habermann, Eppstein (DE); Heinrich Decker, Eppstein (DE); Claus Lattemann, Bad Soden (DE); Oliver Maneg, Frankfurt am Main (AT); Christophe Salagnad, Chatellerault (FR); Frank Zocher, Alsbach-Hahnheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 554 days.

(21) Appl. No.: 11/720,006

(22) PCT Filed: Nov. 18, 2005

(86) PCT No.: PCT/EP2005/012365
§ 371 (c)(1),
(2), (4) Date: Jun. 30, 2008

(87) PCT Pub. No.: WO2006/058620
PCT Pub. Date: Jun. 8, 2006

(65) Prior Publication Data
US 2009/0005299 A1    Jan. 1, 2009

(30) Foreign Application Priority Data
Dec. 1, 2004   (DE) .................... 10 2004 058 306

(51) Int. Cl.
*C12P 21/06*   (2006.01)
*C12N 15/09*   (2006.01)
(52) U.S. Cl. .................................... 435/68.1; 435/69.1
(58) Field of Classification Search .................. None
See application file for complete search history.

(56) References Cited

U.S. PATENT DOCUMENTS

| | | | |
|---|---|---|---|
| 4,708,934 A | | 11/1987 | Gilligan et al. |
| 5,338,833 A | * | 8/1994 | Fowlkes ........................ 530/351 |
| 5,496,924 A | | 3/1996 | Habermann et al. |
| 5,789,234 A | | 8/1998 | Bertelsen et al. |
| 6,255,067 B1 | | 7/2001 | Keutmann et al. |
| 6,319,695 B1 | | 11/2001 | Wong et al. |
| 6,528,486 B1 | * | 3/2003 | Larsen et al. ........................ 514/12 |
| 6,924,264 B1 | * | 8/2005 | Prickett et al. ........................ 514/2 |
| 6,992,172 B1 | * | 1/2006 | Chang et al. ........................ 530/354 |
| 2004/0106547 A1 | | 6/2004 | Larsen et al. |

FOREIGN PATENT DOCUMENTS

| | | | |
|---|---|---|---|
| CA | 1341101 | | 9/2000 |
| EP | 0706066 | | 4/1983 |
| WO | WO 96/04373 | | 2/1996 |
| WO | WO 96/17941 | | 6/1996 |
| WO | WO 00/28067 | | 5/2000 |
| WO | WO01/04156 | * | 1/2001 |

OTHER PUBLICATIONS

Kopeyan et al (FEBS Letters, 1978, vol. 89, pp. 54-58).*
Kaiya et al (Journal of Endocrinology, 2001, vol. 176, pp. 415-423).*
Short et al (Nucleic Acids Research, 1988, vol. 16, pp. 7583-7600).*
Kolhekar et al (Biochemistry, 2002, vol. 41, pp. 12383-12394).*
U.S. Appl. No. 12/065,643, filed Mar. 4, 2008, Sanofi-Aventis Deutschland.
Bradbury et al., Substrate Specificity Of An Amidating Enzyme in Porcine Pituitary, Biochemical and Biophysical Research Communications, vol. 112, No. 2, 1983, pp. 372-377.
Eipper et al., Structure of the Precursor to an Enzyme Mediating COOH-Terminal Amidation in Peptide Biosynthesis, Molecular Endocrinology, vol. 1, No. 11, Nov. 1987, pp. 777-790.
Ishikawa et al., Production of Human Calcitonin in *Escherichia coli* from Multimeric Fusion Protein, J. of Fermentation and Bioengineering, vol. 82, No. 2, 1996, pp. 140-144.
Ohsuye et al., Enhancement of productivity of recombinant alpha-amidating enzyme by low temperature culture, Cytotechnology, vol. 31, 1999, pp. 85-94.
Rourke et al., Heterologous Expression of Human Cholecystokinin in *Saccharomyces cerevisiae*, J. of Biol. Chem., vol. 272, No. 15, Apr. 11, 1997, pp. 9720-9727.
Kulathila, R. et al., "Enzymatic Formation of C-terminal Amides" Natural Product Reports (1999) pp. 145-154, vol. 16.

* cited by examiner

*Primary Examiner* — Karen A Canella
(74) *Attorney, Agent, or Firm* — George Jones, Esq.; Scully, Scott, Murphy & Presser, P.C.

(57) ABSTRACT

The invention relates to the production of carboxy-terminal (C-terminal) amidified peptides with C-terminal amidified lysin, in particular with the biological activity of GLP-1, the chemical and/or biotechnological precursors and intermediate products thereof. The invention also relates to a method for the production and use thereof for producing pharmaceutical products.

26 Claims, No Drawings

METHOD FOR PRODUCING CARBOXY-TERMINAL-AMIDIFIED PEPTIDES

The present invention relates to the production of carboxy-terminal (C-terminal) amidated peptides, with C-terminal amidated lysine, in particular with the biological activity of GLP-1, the chemical or biotechnological precursors and intermediates thereof, methods for the production thereof and uses thereof for the production of pharmaceutical products.

The number of people suffering from diabetes or obesity is increasing with high growth rates throughout the world. It is therefore to be expected that drugs which show high therapeutic benefits in the field of this disease must be made available in increasing quality and quantity.

Patent application US2004/0106547 A1 describes peptides derived from exendin, which on account of their blood sugar-lowering action are of importance as possible drugs in the treatment of diabetes or other metabolic disorders which can for example lead to obesity. In particular, on account of their physiological mechanism of action, it is at present expected that diabetic sequelae will be less marked or much delayed.

The peptides described in US2004/0106547 A1 are found to be particularly active on account of the introduction of one or more C-terminal lysine residues, the terminal one being C-terminal amidated.

For the production of these peptides, various production methods are mentioned in US2004/0106547 A1. One relates to a biotechnological method, wherein, after intracellular expression in yeasts, the target protein is isolated from the cell disintegration product. However, peptides which are C-terminal amidated are only formed in traces by microorganisms, so that biotechnological production as proposed in US2004/0106547 A1 can only be effected very laboriously or cost-intensively.

As an alternative, the application describes the chemical total synthesis of the peptides in question. For this a modified Merryfield synthesis is proposed, which is however still very laborious and is associated with high costs. Among the reasons for this are the fact that the amino acids used for the synthesis must first be produced and purified, in order then after chemical modification to be used specifically in the peptide synthesis as reactants. At the end of the synthesis, the protective groups must be removed and the target peptide or product purified, before it can be formulated as a pharmaceutical. The chemical total synthesis is thus feasible at great expense, and to little ecological advantage.

Enzymes which are capable of amidating peptides at the C terminus have already long been known. These enzymes are called (Eipper et al., Mol. Endocrinol. 1987 November; 1 (11): 1987) peptidylglycine alpha-amidating enzyme (PAM). The production and purification of such PAM enzymes is familiar to the person skilled in the art and has been described in detail; moreover, many such enzyme preparations are commercially available (e.g. K Ohsuye et al., Cytotechnology 31, 1999: 85-94, U.S. Pat. Nos. 4,708,934, 5,789,234, 6,255,067, 6,319,685 and JP0177184).

Bradbury et al. (Biochem. Biophys. Res. Commun. (1983) 112(2): 372-377 showed "in vitro" that PAM preferentially recognizes as substrate peptides whose C terminus consists of the amino acid glycine. They also state that basic amino acids in the N-terminal position to glycine strongly retard the reaction rate of the PAM.

It has now been found that exendin derivatives with a C-terminal sequence of basic amino acids, in particular an oligo- or poly-lysine sequence, which further bear a C-terminal glycine residue, are recognized as substrates surprisingly well by PAM.

Thus surprisingly, according to the invention, biotechnological production of amidated peptides at considerably lower cost is rendered possible, in particular of such amidated peptides as are described in US2004/0106547 A1, whereby the desired product can be prepared by a single enzymatic step from its C-terminal glycine-elongated precursor peptide/protein.

In the process according to the invention, biologically active peptides are produced which contain one or more basic amino acids, preferably lysine, histidine and/or arginine residues, in particular lysine residues with a C terminal lysine residue, wherein the final C-terminal lysine residue is C-terminal amidated. Preferably the peptides produced by the process according to the invention display the biological activity of GLP-1, exendin-4 or biologically active analogs or derivatives thereof.

The present invention thus in particular enables the biotechnological production of the compound No. 2 from US2004/0106547. The said compound No. 2 has the sequence (Seq. ID No.1):

NH$_2$-HGEGTFTSDL SKQMEEEAVR LFIEWLKNGG PSSGAPPSKK KKKK-NH$_2$

Peptides of the formula I are thus objects of the present invention:

wherein
AS is one or more genetically encodable amino acids;
n is 5-2000, preferably 10-1000, in particular 15-500, quite especially preferably 20-400;
X is one or more basic amino acids or derivatives thereof, preferably lysine, histidine and/or arginine, in particular lysine;
m is 1-15, preferably 3-10, in particular 6-8;
Y is one or more neutral charge amino acids, preferably glycine; and
p is 1-10, preferably 1-5, in particular 1;
wherein n, m and p are whole numbers and (AS)n and/or (AS)nXm preferably are a biologically active peptide or protein.

Quite particularly preferred are the compounds of the formula I according to Seq ID No. 2:

NH$_2$-HGEGTFTSDL SKQMEEEAVR LFIEWLKNGG PSSGAPPSKK KKKKG (Seq ID No. 2) and biologically active derivatives thereof with a homology of at least 60%, preferably 80%, in particular 90%.

Also a further object of the present invention are:
a) nucleic acid molecules coding for a peptide according to the invention, preferably DNA, cDNA or RNA molecules;
b) expression cassettes containing the nucleic acid molecules according to the invention;
c) vectors containing the nucleic acid molecules or expression cassettes according to the invention, preferably expression vectors, in particular expression vectors for expression in yeast and/or bacterial cells;
d) host cells containing the nucleic acid molecules, expression cassettes or vectors according to the invention, preferably bacterial or yeast cells, optionally also co-expressing the enzyme PAM;
e) in vitro expression systems which enable the translation of RNA molecules into protein.

Also yet another object of the invention are methods for the production of C-terminal amidated peptides of the general formula II

(AS)n–Xm-NH$_2$ (formula II)

wherein
AS is one or more genetically encodable amino acids;
n is 5-2000, preferably 10-1000, in particular 15-500, quite especially preferably 20-400;
and
(AS)n and/or (AS)n-Xm is a biologically active peptide or protein,
X is one or more basic amino acids or derivatives thereof, preferably lysine, histidine and/or arginine, in particular lysine;
m is 1-15, preferably 3-10, in particular 6-8; and
n and m are whole numbers and wherein
 a) the host cells according to the invention are cultured in a suitable nutrient medium,
 b) the peptides according to the invention are expressed,
 c) optionally the peptides according to the invention are released from a suitable precursor peptide by enzymatic cleavage;
 d) the expression products from step b) or the intermediate products from step c), optionally after purification, are reacted with an alpha-amidating enzyme to give compounds of the general formula II; and
 e) the compounds of the general formula II are purified in a suitable manner, preferably by preparative chromatographic methods.

However, the person skilled in the art is aware that the combinations of known biochemical or biophysical separation methods can also lead to the desired purification result.

Preferably, the process according to the invention is used for the production of C-terminal amidated peptides [for] the production of compounds according to Seq ID No.1.

Firstly, in the context of the process according to the invention, the ability of microorganisms to produce heterologous peptides/proteins is exploited. For this, the desired peptide/protein sequence is translated into the corresponding DNA sequence, which is coupled to a host-specific promoter sequence. Depending on the expression strategy, the target peptide can be expressed here in such a manner that it is formed by the cells directly or indirectly as a fusion protein while remaining intracellular. The fusion protein can either be reacted directly with PAM, before it is processed chemically or enzymatically to the desired target protein, or it is, in the reverse order, first cleaved into the fusion fragments, before the amidation by reaction with PAM takes place. If a fusion strategy is selected, then it is clear to the person skilled in the art that the fusion partners must be linked together via a bridging member which allows the cleavage of the partners in such a manner that the N terminus of the Lys-X$_m$-Gly lengthened target peptide is correctly present after the processing. There are a multitude of options for the design of the bridging member. If for example the amino acid methionine is selected, then chemical cleavage with cyanogen halide is possible. If for example a pentapeptide of the sequence DDDDK is selected as the bridging member, then cleavage with enterokinase is possible. If for example the tetrapeptide sequence IEGR is selected, then the cleavage can be effected via factor Xa. With appropriate design, Genenase® can be used as the processing enzyme for proteins whose N termini begin with histidine. In the examples section below, the cleavage using enterokinase is described.

Alternatively, however, if it is export-compatible, the target peptide can be released into the medium either in the form of a fusion protein, or directly in natural form. For this, cells modified by genetic engineering, in particular of microorganisms, preferably bacteria or yeasts, can be used. If bacterial cells are selected as the expression system, there is also the option of releasing the target protein directly or a corresponding fusion protein which contains the target protein into the periplasm or into the culture medium.

Host organisms and methods in principle available for this are known to the person skilled in the art. These are to a large extent also available commercially from a multitude of suppliers. As typical examples, the firms New England Biolabs, Invitrogen and Roche may be mentioned. In the catalogue descriptions from such firms, there are literature references which provide an overview of the technology.

However it is also clear to the person skilled in the art that the range of the micro-organisms coming into use is constantly being extended, just as is the repertoire of biotechnological methods. Embodiments specialized in this respect are also covered by the object of the present invention.

Typically by way of example the following host/vector systems are mentioned: bacteria of the type *E. coli, S. carnosus, Salmonella, Bacillus subtilis* or *Pseudomonas* and yeasts of the type *K. lactis, P. pastoris, Schizosaccharomyces pombe* and *S. cerevisiae*.

Below, by way of example, the use of systems based on *E. coli* K12 and *E. coli* B is described. The person skilled in the art is however aware that these systems mentioned by way of example offer a multitude of possibilities for variation, which arise for example from the selection of suitable promoters or other regulatory nucleic acid sequences, the genetic properties of the host cell and the vectors used (e.g. copy number of the DNA, selection media, etc.). It is moreover clear to the person skilled in the art that the practical examples described in the text represent only a very small selection in relation to the possibilities actually feasible.

One alternative to the "in vitro" amidation using PAM arises when the enzyme is co-expressed with the precursor protein to be amidated in one and the same host cell. This is achieved by introducing into the host cell the gene sequence which codes for a PAM activity under the control of a host-specific regulation sequence. This expression sequence can either be stably incorporated into the chromosomal DNA sequence in question, or be present on a second plasmid in parallel to the expression plasmid for the target protein, or be integrated as a second expression cassette in one and the same vector, or even be cloned in a polycistronic expression unit in phase with the gene sequence which codes for the target protein under the control of the same promoter sequence.

The present invention thus includes biotechnological methods for the production of peptides of the formula I or derivatives thereof, which display at least 60%, preferably at least 80%, in particular at least 90% homology to the formula I.

The processes according to the invention are characterized in that recombinant organisms are produced which synthesize a peptide precursor which can then be converted into a peptide corresponding to the formula I in the presence of an enzyme directly or by linkage with one or more basic amino acids or derivatives thereof in order, preferably lysine, histidine and/or arginine residues in order, in particular lysine, wherein the sequence is C-terminal amidated.

Further objects of the invention are also the uses of the compounds of formula I or the C-terminal amidated peptides of formula II according to the invention, which have been produced by the method according to the invention, in particular the compounds according to Seq ID No.1 or 2, for the production of a pharmaceutical product or a pharmaceutical formulation, preferably for the treatment of carbohydrate metabolism disorders, particularly preferably for the treatment of diabetes mellitus.

EXAMPLES

Example 1

Synthesis of an *E. coli*-Specific DNA Sequence Coding for AVE$_{1-44}$-Gly

Firstly, the gene sequence Seq ID No.3 coding for the peptide AVE$_{1-44}$-Gly (Seq ID No.2) was prepared:

```
Seq ID No. 3:
TTTTTTAAGCTTG CACGGTGAAG GTACCTTCAC CTCCGACCTG

TCCAAACAGA TGGAAGAAGA AGCTGTTCGT CTGTTCATCG

AATGGCTGAA AAACGGTGGT CCGTCCTCCG GTGCTCCGCC

TTCGAAAAAG AAGAAAAAGA AAGGT TGATA ATAGCATGCA

CGTGCGGCCG CACCTGGTCGA CGAATTCAAA AAAA
```

The synthesis of the gene sequence was effected using PCR technology. For this, the following 5 primers were synthesized by chemical DNA synthesis. This synthesis was effected using the Expedite™ DNA synthesis system.

a) Primer zp5u has the sequence (Seq ID No. 4):
   5'-TTTTTTAAGC TTGCACGGTG AAG-3'

Seq ID No. 4 comprises the region 1-23 of the sense strand.

b) Primer zp3a has the sequence (Seq ID No. 5):
   5'-CTTCCATCTG TTTGGACAGG TCGGAGGTGA AGGTACCTTC

ACCGTGCAAG CTTAAAAAA-3'

Seq ID No. 5 comprises the region 1-59 of the antisense strand.

c) Primer zp3b has the sequence (Seq ID No. 6):
   5'-GGACGGACCA CCGTTTTTCA GCCATTCGAT GAACAGACGA

ACAGCTTCTT CTTCCATCTG TTTGGAGAG-3'

Seq ID No. 6 comprises the region 40-108 of the antisense strand.

d) Primer zp3c has the sequence (Seq ID No. 7):
   5'-GTGCATGCTA TTATCAACCT TTCTTTTTCT TCTTTTTCGA

AGGCGGAGCACCGGAGGACG GACCACCGTT TTTC-3'

Seq ID No. 7 comprises the region 91-164 of the antisense strand.

e) Primer zp3d has the sequence (Seq ID No. 8):
   5'-TTTTTTGAAT TCGTCGACCA GGTGCGGCCG CACGTGCATG

CTATTATCAA CCTT-3'

Seq ID No. 8 comprises the region 144-197 of the antisense strand.

Using the primers, 4 PCR reactions were performed consecutively under standard conditions at 54° C. In reaction 1, 100 ng each of the primers zp3a and zp5u were used. The PCR cycle number was 5. In the second reaction, ¹/₄₀ of the reaction was treated with 100 ng each of the primers zp5u and zp3b in 10 cycles. In reaction 3, ¹/₄₀ of the product of reaction 2 was treated with 100 ng each of the primers zp5u and zp3c in a further 10 cycles. Finally, in 25 PCR cycles with ¹/₄₀ of the product from reaction 3 and the primers zp5u and zp3d, the desired DNA fragment was synthesized, and its length was checked by gel electrophoresis. The desired DNA fragment was purified and reacted with the restriction enzymes EcoR1 and then with Hind3 in accordance with the manufacturers' instructions (New England Biolabs).

In parallel, DNA of the plasmid pUC19 (New England Biolabs) was treated with the enzymes EcoR1 and Hind3. The fragments from the cleavage mixtures were separated by means of a 1.2% agarose gel and then the residual vector fragment from pUC19 and the desired product from reaction 4 were isolated. The purified fragments were ligated together in a T4 ligase reaction overnight at 16° C. Next, competent *E. coli* cells (Stratagene, strain *E. coli* XL10 Gold) were transformed with the ligation mixture and plated out onto agar plates containing 25 mg/l ampicillin. Plasmid DNA was isolated from the individual clones and characterized by DNA sequence analysis.

The plasmid DNA of the desired fragment was named pSCHPUCZP10. It was used as the starting material for the production of expression vectors for the synthesis of the precursor peptides according to the invention in *E. coli* K12 cells.

Example 2

Construction of Expression Vectors which Code for the Precursor Peptide AVE$_{1-44}$-Gly For the production of the peptide AVE$_{1-44}$-Gly, the coding sequence was introduced into the vector pThioHisA from the firm Invitrogen (Catalog No. K360-01). A fusion protein comprising thioredoxin, which is linked with the precursor peptide AVE$_{1-44}$-Gly via the enterokinase recognition sequence DDDDK, was formed. By treatment with enterokinase (Invitrogen), AVE$_{1-44}$-Gly was released and can then be converted into the target protein AVE$_{1-44}$-NH$_2$ in accordance with Example 7 (below) in the presence of PAM (Wako Pure Chemicals Ind. Ltd.).

Two primers with the following sequence were synthesized:

```
Primer Zp_thiohisf with a BamH1 cleavage site (Seq ID No. 9):
5'-TTTTTTGGAT CCGGTGATGA CGATGACAAG CACGGTGAAG GTACCTTC-3'

Primer ZP_thiohisrev with an EcoR1 cleavage site (Seq ID No. 10):
5'-TTTTTTGAAT TCGTCGACCA GGTGC-3'
```

The primers Zp_thiohisf and ZP_thiohisrev were used in a PCR reaction under standard conditions with pSCHPUCZP10 DNA as the template. A PCR fragment was produced, which after cleavage with the enzymes BamH1 and EcoR1 was directly inserted into the pTHIOHisA vector, correspondingly opened with BamH1 and EcoR1, in a T4 ligase reaction. Competent *E. coli* BL21 cells were transformed with the ligation mixture and plated out onto selective agar which contained 25 mg/l ampicillin. The plasmid DNA was reisolated from some clones and analyzed by PCR and subsequent DNA sequence analysis. The desired positive clones, which were named pTHIOHisAZP10-Gly, were analogously checked for expression of the fusion protein in accordance with example 14 of the patent U.S. Pat. No. 5,496,924. On the basis of the positive expression analysis, one clone was selected and fermented for the production of larger quantities of material. The fusion protein formed contains thioredoxin, which is linked with $AVE_{1-44}$-Gly via an enterokinase recognition sequence (Seq ID No. 12).

U.S. Pat. No. 5,496,924, the content whereof is hereby expressly incorporated into the present application by reference, proposes an expression system which in principle enables the production of made-to-measure fusion proteins. The advantage of the system lies in the fact that fusion proteins with a small ballast content can be produced. If the sequence segments A-B are fused with $AVE_{1-44}$Gly via the enterokinase recognition sequence DDDDK, then a fusion protein with the following gene and amino acid sequence (Seq ID No. 11 and 12) is obtained:

```
Seq ID No. 11:
GGAAACAGAATTC ATGGCGCCGA CCTCTTCTTC TACCAAAAAG

CTCAACTGC AACTGGAACA CCTGCTGCTG GACCTGCAGA

TGATCCTGAA CGGTATCAAC AACTACAAAA ACCCGAAACT

GACGCGTATC GACGATGACG ATAAACACGG TGAAGGTACC

TTCACCTCCG ACCTGTCCAA ACAGATGGAA GAAGAAGCTG

TTCGTCTGTT CATCGAATGG CTGAAAAACG GTGGTCCGTC

CTCCGGTGCT CCGCCTTCGA AAAAGAAGAA AAAGAAAGGT

TGATAATAGC ATGCACGTGC GGCCGCAAGC TTAAAAAA

Seq ID No. 12:
MAPTSSSTKK TQLQLEHLLL DLQMILNGIN NYKNPKLTRI

DDDDKHGEGT FTSDLSKQME EEAVRLFIEW LKNGGPSSGA

PPSKKKKKG
```

The preparation of the coding gene sequence was effected by PCR technology. For this the following primers were synthesized:

```
1) Primer psw3_zpcolf (Seq ID No. 13):
5'-CGTATCGACG ATGACGATAA ACACGGTGAA GGTACCTTC-3'
```

The sequence of the primer thus covers the enterokinase recognition site and the start of the $AVE_{1-44}$-Gly coding sequence.

```
2) Primer psw3_zpcolrev (Seq ID No. 14):
5'-GTGTTTATCG TCATCGTCGA TACGCGTCAG TTTCGG-3'
```

The sequence thus corresponds to the synthetic interleukin-2 sequence which according to Table 1 of U.S. Pat. No. 5,496,924 covers the amino acids 34-38 and ⅔ of the codon for the amino acid methionine. The rest of the primer sequence overlaps with primer psw3_zpcolf.

```
3) pBprimef1 (Seq ID No. 15):
5'-TGAGCGGATA ACAATTTCAC AC-3'
```

The primer hybridizes upstream with the EcoR1 cleavage site which is contained in plasmid pK50 (FIG. 33 of U.S. Pat. No. 5,496,924).

```
4) psw3_zp10colrev with Hind3 cleavage site (Seq ID No. 16):
5'-TTTTTTAAGC TTGCGGCCGC ACGTGCATGC TATTATCAAC CTTC-3'
```

Two PCR's were performed in parallel. One was performed on DNA of the plasmid pK50 with the primer pair pBprimef1 and psw3_zpcolrev at 50° C. and the other reaction with the primer pair psw3_zpcolf and psw3_zp10colrev at 54° C. on DNA of the plasmid pTHIOHisAZP10-Gly. The PCR products were purified after gel electrophoresis separation, one aliquot of each were mixed in a 1:1 ratio and then reacted in a third PCR with the primer pair pBprimef1 and psw3_zp10colrev. The PCR product was treated with the enzymes EcoR1 and Hind3 and inserted into the plasmid pK50, opened in parallel with these enzymes, in a T4 ligase reaction. Competent *E. coli* BL21 cells were transformed with the ligation mixture and plated out onto selective agar which contained 25 mg/l ampicillin. Plasmid DNA was reisolated from some clones and analyzed by PCR and subsequent DNA sequence analysis. Positive clones were named pBZP100 and were checked for expression of the fusion protein.

The expression products were analyzed by mass spectrometry and by SDS-PAGE and the N terminus determined by protein sequence analysis.

A suitable clone was selected for the fermentation of larger quantities of material.

Example 3

Fermentation of the Strains Constructed in Example 2

*E. coli* BL21 cells, transformed with different plasmid vectors coding for target peptide derivatives (fusion protein) were cultured in a fermenter in mineral salt medium or complex medium (see Example 1) at 30° C. or 37° C. and a pH of 7.0. The pH adjustment was effected using an $NH_4^+$ solution (26% in water). The aeration of the culture was ensured through a control strategy which kept the dissolved oxygen in the culture broth constant at 30%. For fed batch processes in mineral salt medium, a glucose solution (60% w/v) was fed in (8 g/L/hr to 26 g/L/hr) after completion of the batch phase. The induction of protein expression was effected by the addition of IPTG (1-4 mM final concentration (f.c.)). The duration of the induction was 6-8 hrs. The expression of the target proteins was detected by SDS polyacrylamide gel electrophoresis (SDS-PAGE).

The expression of $AVE_{1-44}$-Gly(-fusion protein) in *E. coli* BL21/pBZP100 was carried out as described below:

100 µL of cell suspension were withdrawn from a permanent culture of *E. coli* BL21 cells stored at −80° C., and incubated for 10-16 hrs with shaking at 37° C. in 0.5 L of preculture medium. The main culture in the fermenter was inoculated to an inoculation density of 0.01 to 0.05 $OD_{600}$ with the appropriate quantity of preculture.

Preculture Medium:
5 g/L Bacto tryptone
10 g/L yeast extract
5 g/L NaCl

Main Culture Medium:
Defined mineral salt medium (minimal medium) based on glucose as the carbon source (Jeffrey H Miller: Experiments in Molecular Genetics, Cold Spring Harbor Laboratory (1972)).

After consumption of the glucose initially present in the main culture medium, a glucose solution was fed in. Protein expression induced by addition of IPTG (1 mM f.c.) and the maximal expression of the fusion protein after the induction observed.

Using for example the SDS-PAGE analysis system from the firm Novex (NuPage® Novex 12% gel system, Invitrogen™), 0.02 $OD_{600nm}$ portions of cell suspension, which had been withdrawn from the fermenter at different culture time points, were analyzed in accordance with the manufacturer's instructions.

Example 4

Purification of the Fusion Protein

Isolation of the BZP-$AVE_{1-44}$-Gly Fusion Protein:
200 g of biomass of a recombinant *E. coli* strain were resuspended in 300 ml of Tris buffer (50 mM Tris/HCl, pH 7.4; 1 mM EDTA). Cell disintegration was performed by twofold high pressure homogenization (Rannie high pressure homogenizer, 1000 bar). Insoluble components in the homogenizate were removed by centrifugation. The supernatant was filtered under pressure (Sartorius 0.22 μm filter, type 111) and applied onto a chromatography column (Source S, Amersham Biosciences) previously equilibrated with buffer (50 mM Tris/HCl pH 7.3; 1 mM EDTA). After the sample had been applied, a washing step was effected with equilibration buffer (2 column volumes), followed by a further washing step with 10% high salt buffer (50 mM Tris/HCl pH 7.3; 1 M NaCl, 1 mM EDTA). The fractionation was effected by application of a salt gradient using high salt buffer over 5 column volumes. The fusion protein content of the individual fractions was tested by SDS gel electrophoresis (NuPage® Novex 12% gel system, Invitrogen). Fusion protein-containing fractions were combined and concentrated between 5- and 10-fold (Millipore ultrafiltration cell, 10 kDa cut-off membrane). The concentrate was used directly for the protease cleavage reaction by buffer exchange into enterokinase buffer (50 mM Tris/HCl pH 7.4; 50 mM NaCl, 2 mM $CaCl_2$), or further purified by gel filtration (Superdex 75, Amersham Biosciences) before the cleavage reaction.

The cleavage of the fusion proteins was effected with enterokinase (Invitrogen) in enterokinase buffer (20 mM Tris/HCl, 50 mM NaCl, 2 mM $CaCl_2$ pH 7.4) in accordance with the manufacturer's instructions.

Example 5

Purification of a Thioredoxin Fusion Protein Containing Seq ID No.3

200 g of biomass of a recombinant *E. coli* strain were resuspended in 50 mM Tris buffer (pH 7.4; 1 mM EDTA). Cell disintegration was performed by twofold high pressure homogenization (Rannie high pressure homogenizer, 1000 bar). Insoluble components in the homogenizate were removed by centrifugation. The supernatant was filtered under pressure (Sartorius 0.22 μm filter, type 111) and applied onto a chromatography column (Source Q, Amersham Biosciences) previously equilibrated with buffer (50 mM Tris/HCl pH 7.4; 1 mM EDTA). After the sample had been applied, a washing step was effected with equilibration buffer (2 column volumes), and the fractionation was effected by application of a salt gradient using high salt buffer (50 mM Tris/HCl pH 7.4; 0.3 M NaCl, 1 mM EDTA) over 6 column volumes. The fusion protein content of the individual fractions was tested by SDS gel electrophoresis (NuPage® Novex 12% gel system, Invitrogen™). Fusion protein-containing fractions were combined and concentrated 5- to 10-fold (Millipore ultrafiltration cell, 10 kDa cut-off membrane). The concentrate was further fractionated by gel filtration chromatography (Superdex 75, Amersham Biosciences). A previously equilibrated column (50 mM Tris/HCl pH 7.4; 200 mM NaCl) was loaded with up to 5% of the column volume with concentrated fusion protein solution. The elution is effected by rinsing with equilibration buffer. The fusion protein content of the individual fractions was again tested by SDS gel electrophoresis ((NuPage® Novex 12% gel system, Invitrogen™. The relevant fractions were combined, concentrated to ca. 5 mg/ml (Vivaspin concentrators with 10 kD cut-off, Vivascience) and the buffer exchange into enterokinase buffer (20 mM Tris/HCl pH 7.4; 50 mM NaCl) was effected by means of diafiltration units (Vivascience).

The processing of the $AVE_{1-44}$-Gly precursor stage was then effected using enterokinase analogously to Example 4.

Example 6

Separation of the Cleavage Products from the Enterokinase Cleavage Reaction

After the cleavage of the fusion proteins using enterokinase, the cleavage products were separated from one another by ion exchange chromatography (Source 30S, Amersham Biosciences). The ionic strength of the solution was adjusted to ca. 10 mS/cm by addition of sodium chloride. After application of the protein solution onto the previously equilibrated column (20 mM Tris/HCl, pH 7.4; adjusted with NaCl to a conductivity of ca. 10 mS/cm), unbound material was washed out with buffer (20 mM Tris/HCl, pH 7.4; adjusted with NaCl to a conductivity of ca. 10 mS/cm). The elution of the $AVE_{1-44}$-Gly peptide was effected by application of a gradient to 500 mM NaCl over 10 column volumes.

The identification of $AVE_{1-44}$-containing fractions or precursor stages to AVE-1-44 was effected by SDS gel electrophoresis, HPLC and mass spectrometry. The appropriate fractions were combined and lyophilized after removal of organic solvent.

Finally, to confirm the amino acid sequence, the $AVE_{1-44}$-Gly isolated was totally sequenced via Edman.

Example 7

Conversion of $AVE_{1-44}$-Gly into $AVE_{1-44}$-$NH_2$

The reaction was performed using the enzyme PAM (peptidyl-glycine-amidating enzyme Wako Pure Chemicals Ind., Ltd. (Ordering No. 161-16971)) in accordance with the manufacturer's instructions concerning the reaction conditions.

The following solution was made up:
1 µM CuSO₄
5 mM KI
3 mM Na ascorbate
230 U/ml catalase (bovine, Fluka)
600 U/ml PAM (Wako Chemicals)
0.1 M Tris/HCl pH 7.0 with 0.001% Triton X-100

The solution was preincubated for 1 hr at 37° C. and then the $AVE_{1-44}Gly$ protein solution (Tris/HCl pH 7.0, 80 µg/ml final concentration) was added. The reaction mixture was then further incubated at 37° C. The course of the reaction was followed by sampling at different times. At maximal conversion, the reaction was stopped by addition of a 50 mM EDTA solution.

The reaction mixture was then separated by ion exchanger chromatography (Shodex Co., column type IEC CM-825 (8×75 mm)). The following gradient was applied to this column:

Eluent A—40 mMol phosphate buffer pH 7+20% acetonitrile
Eluent B—50 mMol phosphate buffer pH 7+1 M NaCL The column was operated at room temperature with a throughflow rate of 2 ml/min or 1 ml/min.

The eluted fractions (detection at 280 nm) were collected and the mass of the relevant peptide determined by MALDI-MS. The mass spectrometric analyses were performed with an instrument of the BRUKER Reflex IV type. The samples were used directly for the MALDI-MS analysis, or diluted to a concentration of ca. 50 µmol/µl with 50% TAaq ([1+1] 0.1% TFA+50% acetonitrile).

The expected mass for the $AVE_{1-44}\text{-}NH_2$ was confirmed. The product obtained can be supplied for further pharmaceutical use.

Pharmaceutical formulations can thereafter be produced in a manner known to the person skilled in the art by addition of suitable pharmaceutical formulation additives to the biologically active peptide or peptide derivative.

The invention claimed is:

1. A method for the production of C-terminal amidated peptides of the general formula II:

(AS)n-Xm-NH2    (formula II)

wherein

AS is a genetically encoded amino acid;
n is 5-2000;
and
X is a basic amino acid or derivatives thereof,
m is 1-15; and
n and m are whole numbers and wherein
i) a host cell transformed with an expression cassette, vector or an in vitro expression system, each containing a nucleic acid sequence encoding formula I:

(AS)n$_2$-Xm$_2$-Yp    (formula I)

wherein

AS is a genetically encodable amino acid;
X$_2$ is a basic amino acid or derivatives thereof;
m$_2$ is 1-15
Y is at least one neutral charge amino acid;
p is 1-10;
wherein n$_2$, m$_2$ and p are whole numbers;
is cultured in a nutrient medium,
ii) the nucleic acid sequence is expressed,
iii) optionally the expressed compounds are released from a precursor peptide by enzymatic or chemical cleavage,
iv) the expression products from ii) or the intermediate products from iii) are reacted with an alpha-amidating enzyme after an optional purification step, and
v) the C-terminal amidated peptide of the general formula II is purified.

2. A method according to claim 1 wherein said expressed compounds are released from precursor peptides by enterokinase.

3. The method according to claim 1, wherein n is 10-1000.
4. The method according to claim 1, wherein n is 15-500.
5. The method according to claim 1, wherein n is 20-400.
6. The method according to claim 1, wherein at least one of (AS)n and (AS)n-Xm is a biologically active peptide or protein.
7. The method according to claim 1, wherein X is selected from the group consisting of histidine, arginine and lysine.
8. The method according to claim 1, wherein X is lysine.
9. The method according to claim 1, wherein m is 3-10.
10. The method according to claim 1, wherein m is 6-8.
11. The method according to claim 1, wherein n$_2$ is 10-1000.
12. The method according to claim 1, wherein n$_2$ is 15-500.
13. The method according to claim 1, wherein n$_2$ is 20-400.
14. The method according to claim 1, wherein X$_2$ is selected from the group consisting of histidine, arginine and lysine.
15. The method according to claim 1, wherein X$_2$ is lysine.
16. The method according to claim 1, wherein m$_2$ is 1-15.
17. The method according to claim 1, wherein m$_2$ is 3-10.
18. The method according to claim 1, wherein m$_2$ is 6-8.
19. The method according to claim 1, wherein Y is glycine.
20. The method according to claim 1, wherein p is 1-5.
21. The method according to claim 1, wherein p is 1.
22. The method according to claim 1, wherein the general formula II is purified by a preparative chromatographic method.

23. The method according to claim 1, wherein the nucleic acid is DNA.

24. The method according to claim 1, wherein the nucleic acid is RNA.

25. The method according to claim 1, wherein formula 2 is according to SEQ ID NO. 1.

26. The method according to claim 1, wherein at least one of $(AS)n_2$ and $(AS)n_2$-$Xm_2$ is a biologically active peptide or protein.

* * * * *

SEQUENCE LISTING

```
<160> NUMBER OF SEQ ID NOS: 16

<210> SEQ ID NO 1
<211> LENGTH: 44
<212> TYPE: PRT
<213> ORGANISM: Artificial Sequence
<220> FEATURE:
<223> OTHER INFORMATION: Description of the artificial sequence:
      synthetic Peptide;MOD_RES K44 Amidation

<400> SEQUENCE: 1

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Lys Lys Lys Lys Lys Lys
         35                  40

<210> SEQ ID NO 2
<211> LENGTH: 45
<212> TYPE: PRT
<213> ORGANISM: Artificial Sequence
<220> FEATURE:
<223> OTHER INFORMATION: Description of the artificial sequence:
      synthetic Peptide

<400> SEQUENCE: 2

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Ser Lys Lys Lys Lys Lys Lys Gly
         35                  40                  45

<210> SEQ ID NO 3
<211> LENGTH: 198
<212> TYPE: DNA
<213> ORGANISM: Artificial Sequence
<220> FEATURE:
<223> OTHER INFORMATION: Description of the artificial sequence:
      synthetic DNA

<400> SEQUENCE: 3 tttttttaagc ttgcacggtg aaggtacctt cacctccgac ctgtccaaac agatggaaga      60
```

-continued

```
agaagctgtt cgtctgttca tcgaatggct gaaaaacggt ggtccgtcct ccggtgctcc    120
gccttcgaaa aagaagaaaa agaaaggttg ataatagcat gcacgtgcgg ccgcacctgg    180
tcgacgaatt caaaaaaa                                                  198

<210> SEQ ID NO 4
<211> LENGTH: 23
<212> TYPE: DNA
<213> ORGANISM: Artificial Sequence
<220> FEATURE:
<223> OTHER INFORMATION: Description of the artificial sequence:Primer

<400> SEQUENCE: 4 tttttaagc ttgcacggtg aag                                              23

<210> SEQ ID NO 5
<211> LENGTH: 59
<212> TYPE: DNA
<213> ORGANISM: Artificial Sequence
<220> FEATURE:
<223> OTHER INFORMATION: Description of the artificial sequence:Primer

<400> SEQUENCE: 5
cttccatctg tttggacagg tcggaggtga aggtaccttc accgtgcaag cttaaaaaa     59

<210> SEQ ID NO 6
<211> LENGTH: 69
<212> TYPE: DNA
<213> ORGANISM: Artificial Sequence
<220> FEATURE:
<223> OTHER INFORMATION: Description of the artificial sequence:Primer

<400> SEQUENCE: 6
ggacggacca ccgttttca gccattcgat gaacagacga acagcttctt cttccatctg    60
tttggacag                                                            69

<210> SEQ ID NO 7
<211> LENGTH: 74
<212> TYPE: DNA
<213> ORGANISM: Artificial Sequence
<220> FEATURE:
<223> OTHER INFORMATION: Description of the artificial sequence:Primer

<400> SEQUENCE: 7
gtgcatgcta ttatcaacct ttcttttct tcttttcga aggcggagca ccggaggacg      60
gaccaccgtt tttc                                                      74

<210> SEQ ID NO 8
<211> LENGTH: 54
<212> TYPE: DNA
<213> ORGANISM: Artificial Sequence
<220> FEATURE:
<223> OTHER INFORMATION: Description of the artificial sequence:Primer

<400> SEQUENCE: 8
ttttttgaat tcgtcgacca ggtgcggccg cacgtgcatg ctattatcaa cctt          54

<210> SEQ ID NO 9
<211> LENGTH: 48
<212> TYPE: DNA
<213> ORGANISM: Artificial Sequence
<220> FEATURE:
<223> OTHER INFORMATION: Description of the artificial sequence:Primer

<400> SEQUENCE: 9
```

```
tttttttggat ccggtgatga cgatgacaag cacggtgaag gtaccttc                48
```

<210> SEQ ID NO 10
<211> LENGTH: 25
<212> TYPE: DNA
<213> ORGANISM: Artificial Sequence
<220> FEATURE:
<223> OTHER INFORMATION: Description of the artificial sequence:Primer

<400> SEQUENCE: 10

```
tttttttgaat tcgtcgacca ggtgc                                        25
```

<210> SEQ ID NO 11
<211> LENGTH: 321
<212> TYPE: DNA
<213> ORGANISM: Artificial Sequence
<220> FEATURE:
<223> OTHER INFORMATION: Description of the artificial sequence:
      synthetic DNA

<400> SEQUENCE: 11

```
ggaaacagaa ttcatggcgc cgacctcttc ttctaccaaa aagactcaac tgcaactgga    60
acacctgctg ctggacctgc agatgatcct gaacggtatc aacaactaca aaacccgaa    120 actgacgcgt atcgacgatg acgataaaca cggtgaaggt accttcacct ccgacctgtc   180
caaacagatg gaagaagaag ctgttcgtct gttcatcgaa tggctgaaaa acggtggtcc   240
gtcctccggt gctccgcctt cgaaaaagaa gaaaaagaaa ggttgataat agcatgcacg   300
tgcggccgca agcttaaaaa a                                             321
```

<210> SEQ ID NO 12
<211> LENGTH: 90
<212> TYPE: PRT
<213> ORGANISM: Artificial Sequence
<220> FEATURE:
<223> OTHER INFORMATION: Description of the artificial sequence:
      synthetic Peptide

<400> SEQUENCE: 12

```
Met Ala Pro Thr Ser Ser Ser Thr Lys Lys Thr Gln Leu Gln Leu Glu
 1               5                  10                  15

His Leu Leu Leu Asp Leu Gln Met Ile Leu Asn Gly Ile Asn Asn Tyr
            20                  25                  30

Lys Asn Pro Lys Leu Thr Arg Ile Asp Asp Asp Lys His Gly Glu
        35                  40                  45

Gly Thr Phe Thr Ser Asp Leu Ser Lys Gln Met Glu Glu Glu Ala Val
    50                  55                  60

Arg Leu Phe Ile Glu Trp Leu Lys Asn Gly Gly Pro Ser Ser Gly Ala
65                  70                  75                  80

Pro Pro Ser Lys Lys Lys Lys Lys Lys Gly
                85                  90
```

<210> SEQ ID NO 13
<211> LENGTH: 39
<212> TYPE: DNA
<213> ORGANISM: Artificial Sequence
<220> FEATURE:
<223> OTHER INFORMATION: Description of the artificial sequence:Primer

<400> SEQUENCE: 13

```
cgtatcgacg atgacgataa acacggtgaa ggtaccttc                           39
```

```
<210> SEQ ID NO 14
<211> LENGTH: 36
<212> TYPE: DNA
<213> ORGANISM: Artificial Sequence
<220> FEATURE:
<223> OTHER INFORMATION: Description of the artificial sequence:Primer

<400> SEQUENCE: 14
gtgtttatcg tcatcgtcga tacgcgtcag tttcgg                            36

<210> SEQ ID NO 15
<211> LENGTH: 22
<212> TYPE: DNA
<213> ORGANISM: Artificial Sequence
<220> FEATURE:
<223> OTHER INFORMATION: Description of the artificial sequence:Primer

<400> SEQUENCE: 15
tgagcggata acaatttcac ac                                           22

<210> SEQ ID NO 16
<211> LENGTH: 44
<212> TYPE: DNA
<213> ORGANISM: Artificial Sequence
<220> FEATURE:
<223> OTHER INFORMATION: Description of the artificial sequence:Primer

<400> SEQUENCE: 16 tttttttaagc ttgcggccgc acgtgcatgc tattatcaac cttc                  44
```